(12) United States Patent
Bitzer (10) Patent No.: US 9,955,917 B2
(45) Date of Patent: May 1, 2018

(54) PLANAR LOGIC BOARD FOR ABLATION CATHETER WITH FORCE MEASUREMENT FUNCTIONALITY

(71) Applicant: VascoMed GmbH, Binzen (DE)

(72) Inventor: Andreas Bitzer, Zurich (CH)

(73) Assignee: VascoMed GmbH, Binzen (DE)

( * ) Notice: Subject to any disclaimer, the term of this patent is extended or adjusted under 35 U.S.C. 154(b) by 433 days.

(21) Appl. No.: 14/709,746

(22) Filed: May 12, 2015

(65) Prior Publication Data

US 2015/0359484 A1 Dec. 17, 2015

Related U.S. Application Data

(60) Provisional application No. 62/010,466, filed on Jun. 11, 2014.

(51) Int. Cl.
| | | |
|---|---|---|
| A61B 5/00 | (2006.01) | |
| A61N 1/05 | (2006.01) | |
| A61B 18/14 | (2006.01) | |
| A61N 1/06 | (2006.01) | |
| G01L 1/24 | (2006.01) | |
| A61B 17/00 | (2006.01) | |
| A61B 18/00 | (2006.01) | |
| A61B 90/00 | (2016.01) | |
| A61B 34/20 | (2016.01) | |

(52) U.S. Cl.
CPC ............ *A61B 5/68* (2013.01); *A61B 18/1492* (2013.01); *A61N 1/05* (2013.01); *A61N 1/056* (2013.01); *A61N 1/06* (2013.01); *G01L 1/246* (2013.01); *A61B 2017/00061* (2013.01); *A61B 2018/00178* (2013.01); *A61B 2018/1465* (2013.01); *A61B 2034/2061* (2016.02); *A61B 2090/064* (2016.02); *A61B 2090/065* (2016.02); *A61B 2562/0266* (2013.01); *A61B 2562/227* (2013.01)

(58) Field of Classification Search
None
See application file for complete search history.

(56) References Cited

U.S. PATENT DOCUMENTS

| | | |
|---|---|---|
| 5,343,860 A | 9/1994 | Metzger et al. |
| 8,286,510 B2 | 10/2012 | Meiss et al. |
| 2003/0018273 A1 | 1/2003 | Corl et al. |
| 2008/0085074 A1 | 4/2008 | Wakahara et al. |
| 2008/0285909 A1 | 11/2008 | Younge et al. |
| 2012/0265102 A1 | 10/2012 | Leo et al. |

FOREIGN PATENT DOCUMENTS

| | | |
|---|---|---|
| WO | 2008003307 | 1/2008 |
| WO | 2009007857 | 1/2009 |
| WO | 2010088922 | 8/2010 |
| WO | 2015059311 | 4/2015 |

OTHER PUBLICATIONS

European Search Report and Annex to the European Search Report on European Patent Application No. EP 15 16 8296, dated Nov. 4, 2015 (6 pages).

*Primary Examiner* — Brian T Gedeon
(74) *Attorney, Agent, or Firm* — Buchanan Ingersoll & Rooney PC (57) ABSTRACT

A sensor connection element of a catheter or an electrode line, which has a plate-like substrate including at least one recess and layer-like electrical conductors with sensor connection faces and/or actuator connection faces on or beneath at least one sensor surface.

15 Claims, 6 Drawing Sheets

PLANAR LOGIC BOARD FOR ABLATION CATHETER WITH FORCE MEASUREMENT FUNCTIONALITY

CROSS-REFERENCE TO RELATED APPLICATIONS

This patent application claims the benefit of co-pending U.S. Provisional Patent Application No. 62/010,466, filed on Jun. 11, 2014, which is hereby incorporated by reference in its entirety.

TECHNICAL FIELD

The present invention relates to a sensor connection element of a catheter or an electrode line and to a catheter and an electrode line containing such a sensor connection element. The term "sensor connection element" is to be understood hereinafter on the one hand as a connection element of a sensor in a catheter or an electrode line, but also additionally in the sense of a sensor element/connection element, that is to say in a broader sense primarily as a sensor element, but also as a connection element, independent of sensor functions, belonging to other functional units of a catheter or an electrode line, in particular, of stimulation or ablation electrodes or other actuators.

BACKGROUND

The starting point of the present invention lies in the specialist medical field of what are known as ablation catheters, with which areas of biological tissue can be cauterized or tissue parts can be removed, and even more specifically in ablation catheters with contact force measurement.

An ablation catheter (e.g., "TactiCath", manufactured by Endosense) is known which enables the measurement of a force acting on the distal catheter end (that is to say of the aforementioned contact force during use) in terms of magnitude and direction during an ablation procedure. This catheter uses the principle of what is known as an FBG ("Fiber Bragg Grating") sensor, wherein three fibers, each with an FBG sensor at the fiber end, form the group of sensors required for a 3-dimensional ("3D") force measurement and can be connected to a signal processing unit for joint measurement signal processing. The sensors are fitted externally on a deformable cylinder with an angular spacing of 120°.

In U.S. Publication No. 2008/0285909, the operating principle of FBG sensors for determining twists or curvatures of the catheter body is described in detail, and the operating principle of the aforementioned force sensor comprising a plurality of FBG fibers on a deformable cylinder is also explained in this document.

In European Patent No. 2 491 883, which can be traced back to the Applicant, an ablation catheter of simplified structure with contact force measurement is described, said ablation catheter containing an individual FBG fiber comprising a plurality of sensor regions distanced from one another in the longitudinal direction. These sensor regions are arranged and formed and suitably read out in such a way that the spatial force components of a force acting on the catheter end can be determined; and additionally it is also possible to obtain temperature signals for the correction of the force measurement signals.

Independently of this measuring principle, other solutions for a contact force measurement on a guide wire or catheter are also known, for example, with use of an optical sensor, as described in International Publication No. WO2009/007857, or with use of a semiconductor sensor at the tip of a guide wire, as described in International Publication No. WO2008/003307.

Multi-axis force sensors and torque sensors have long been known in a wide range of embodiments outside the aforementioned technical field, and there are also embodiments in which printed circuit boards are used; see e.g., International Publication No. WO2010/088922.

With the construction of sensor connection elements of the aforementioned type that are suitable for series production, it has been found that the previously known superstructures are not optimal from a technological viewpoint and, in particular, impose certain limits on the automation of the production, thus leading to relatively high production costs.

The present invention is directed toward overcoming one or more of the above-mentioned problems.

SUMMARY

An object of the present invention is therefore to provide a sensor connection element that is improved, in particular, in terms of its suitability for series production and, therefore, in terms of the production costs and, therefore, ultimately to also provide a less costly catheter or an electrode line comprising such a sensor connection element.

At least this object is achieved in principle by a sensor connection element having the features of claim 1 and, in terms of the medical products derived therefrom, by a catheter having the features of claim 12, or an electrode line having the features of claim 13. Expedient developments of the inventive concept are disclosed in the respective dependent claims.

Besides the above-mentioned finding, the present invention includes the notion of proceeding from a plate-like substrate, which is planar at least in the production process, and layer-like electrical conductors with sensor connection faces and/or actuator-connection faces on or beneath at least one sensor surface.

Compared with known constructions, this allows a reduced complexity of the production process and a largely automated production, with use of known photolithographic techniques and commercially conventional assembly machines. The processes can be largely parallelized.

Furthermore, in view of a reliable function and long-term stability of the finished product, in particular, of force transducer elements structured in accordance with the present invention, a key advantage can be considered to be lower demands on the manufacturing tolerance. With the structure according to the present invention, surfaces sliding over one another, in particular, cylinder surfaces, are avoided in principle, whereby demands in terms of the production tolerance of the matching cylinder dimensions are eliminated. Since each sensor (in particular, force transducer) produced in accordance with the present invention is typically calibrated individually, manufacturing tolerances on the whole are less decisive than with known products.

Previous force measurement catheters and similar products have the problem that a very large number of electrical lines and tubes are laid in a very confined space and do not behave linearly with respect to deformation. Since the measurement method with strain measurement is based on deformation, these effects have an interfering effect. With the structure according to the present invention described herein, lines are extremely miniaturized and, therefore, these interferences are significantly reduced.

Currently conventional catheters are assembled by hand, and the catheter is composed of a number of component parts. Since the production by hand causes a relatively high tolerance compared to the accuracy that can be achieved with machines, the rejection rate is relatively high. The present invention described here makes it possible to replace the manual assembly process by an injection molding method.

Conventional electrode lines for cardiac pacemakers and automatic defibrillators are provided with fine metal rings for the dissipation of heart signals. These have to be threaded on and wired by hand. The present invention presented here makes it possible, in a specific embodiment, for the electrodes to be pre-formed in a technically simple manner as planar conductor lugs, and to be positioned fully automatically in a wired manner and fitted on the line body.

In a first exemplary embodiment of the present invention, the plate-like substrate is flat in the state of use. Alternatively, the plate-like substrate may be curved in the state of use, in particular, into the shape of a hollow cylinder or hollow cylinder portion. With the production of a catheter or an electrode line, which typically have a cylindrical outer shape, the substrate can thus be arranged radially on the one hand and on the other hand can bear against the inner wall of the line body.

In a further exemplary embodiment of the present invention, the substrate is structured in a multi-layered manner and has two or more levels, in which layer-like electrical conductors are arranged. Due to the provision of a number of line levels, a plurality of different signals can be transmitted without interference, as is known per se from the field of electrical circuit boards.

In a further exemplary embodiment of the invention, the substrate is formed from a material that is rigid in compression and has at least one recess in both side edges and in at least one surface, said recesses providing the sensor connection element with a predetermined flexural resilience. This is an embodiment that is specifically suitable for forming a force measurement sensor and, therefore, ultimately for producing a force measurement catheter. In order to provide the functionality, recesses that are offset relative to one another in the longitudinal direction of the substrate and that extend over the central line are provided, in particular, in the side edges in such a way that the sensor connection element has a predetermined compressive resilience with respect to forces acting in the longitudinal direction.

In accordance with a further exemplary embodiment, the recess or at least one of a number of recesses has a rectangular or trapezoidal cross section.

In view of different exemplary embodiments and functions of the products structured in accordance with the present invention, expedient embodiments in terms of material may be those in which the substrate comprises a metal or semiconductor material, in particular, silicon, and/or a ceramic, in particular, alumina ceramic, and/or a plastic material, in particular, epoxy resin. The selection of the specific material may be just as dependent on the technological possibilities of a manufacturer as on the overall dimensions of the product or cost limits.

An embodiment currently deemed to be very beneficial is one in which an FBG sensor is fitted on the substrate so as to be arranged parallel to the side edges and is read in such a way that the sensor connection element forms a 3D force sensor. In accordance with an alternative embodiment of a force measurement sensor, the layer-like conductors are formed on the substrate and are selectably provided with additional functional elements in such a way that the sensor connection element forms an electric strain gauge.

Especially in view of the technically simple and cost-effective manufacture of electrode lines, an embodiment in which a conductor lug is fitted on at least one actuator connection face so as to provide a sensing and/or stimulation electrode of an electrode line is of particular interest. With an ablation electrode line, a connection face for an ablation electrode can be fitted close to a short side face of the substrate, which comes to rest during use at the distal end of the catheter.

In one exemplary embodiment of the electrode line fitted with the sensor connection element according to the present invention, the line body is compressible and flexible in a distal portion, in which the sensor connection element is arranged, in such a way that it does not falsify the response of the 3D force sensor or strain gauge to external forces.

In an exemplary embodiment of this electrode line that builds on an embodiment described further above of the sensor connection element, the line has at least one ring electrode, which is formed by winding a conductor lug, applied to an actuator connection face of the sensor connection element, around the line body.

Further features, aspects, objects, advantages, and possible applications of the present invention will become apparent from a study of the exemplary embodiments and examples described below, in combination with the Figures, and the appended claims.

DESCRIPTION OF THE DRAWINGS

Advantages and expedient features of the present invention will also emerge from the following description of an exemplary embodiment with reference to the Figures, in which.

DETAILED DESCRIPTION

Figure 1A:
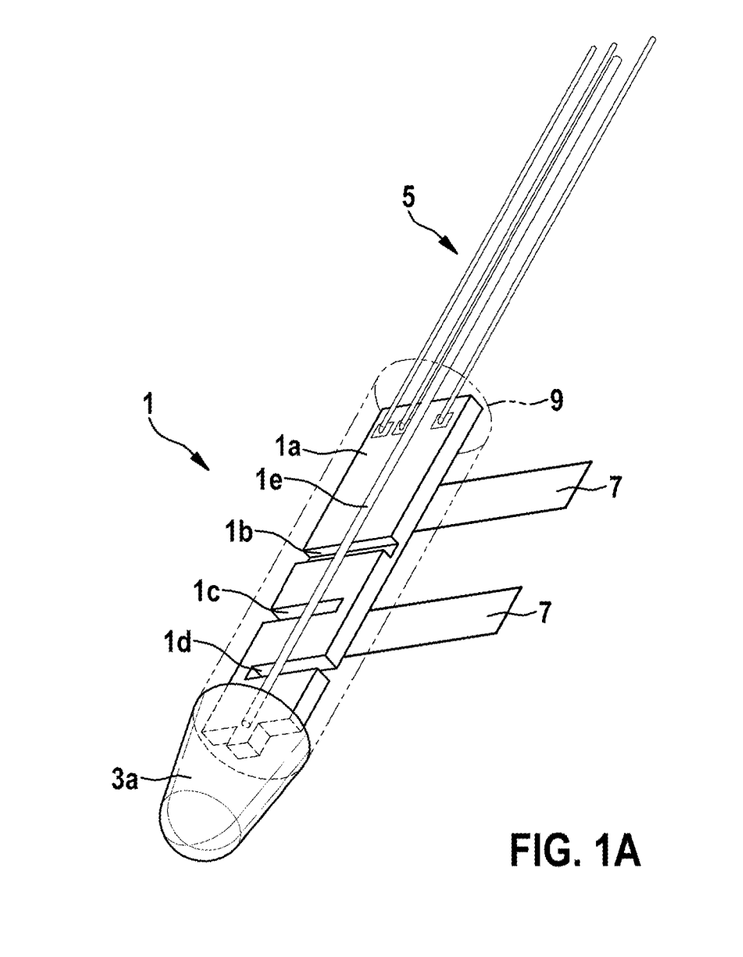
FIGS. 1A and 1B show perspective views of a schematic overall view of a sensor connection element and of a distal end portion of a corresponding ablation catheter according to the present invention in the embodiment in the form of a force transducer element, for example in an ablation electrode line.

FIG. 1A shows a planar force transducer element 1, mounted on a catheter tip 3a of an ablation electrode line (not visible in this Figure) and provided with feed lines 5 that are soldered on, or bonded on, and also provided with two conductor lugs 7 pressed onto the rear side. A resilient plastic overmoulding 9 provided in the state of use is illustrated by a dashed line. The force transducer element 1 basically comprises a plate-shaped substrate 1a having three recesses (for example, milled-out portions or recesses created by laser) 1b, 1c and 1d, which are each rectangular in cross section, and an FBG sensor 1e laid fixedly and centrally in the longitudinal extension of the substrate. Further explanations concerning the structure and operating principle of the force transducer can be found further below.

Figure 1B:
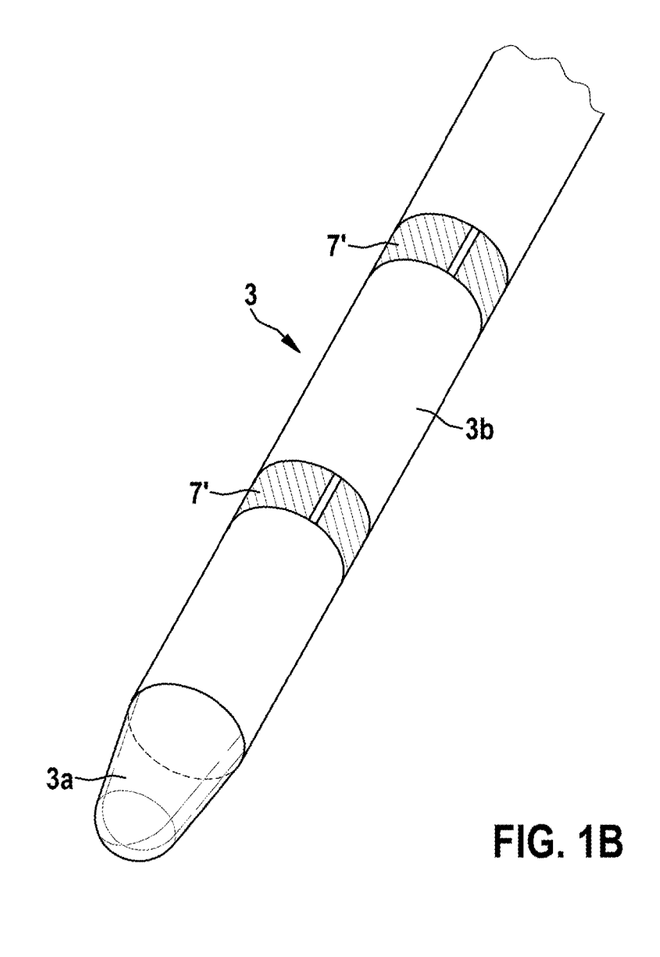

FIG. 1B shows an external view of the distal end portion of an ablation electrode line 3 with the aforementioned catheter tip 3a, which is operatively connected to the force transducer, and an adjoining resilient line body 3b, for example, made of a silicone material conventional for catheters or electrode lines. Two ring electrodes 7' are arranged on the line body 3b at a distance from the catheter tip 3a or the distal end and at a distance from one another, and are formed by winding the conductor lugs 7 shown in FIG. 1A around the line body. For the rest, ablation electrode lines and ablation catheters are known per se and, therefore, a more detailed description is not necessary herein. However, it is noted that, for the exemplary embodiment with an integrated force transducer according to FIG. 1A, a sufficiently resilient encasement is necessary so as not to adversely influence the sensing characteristics of the force transducer or strain gauge.

Figure 2A:
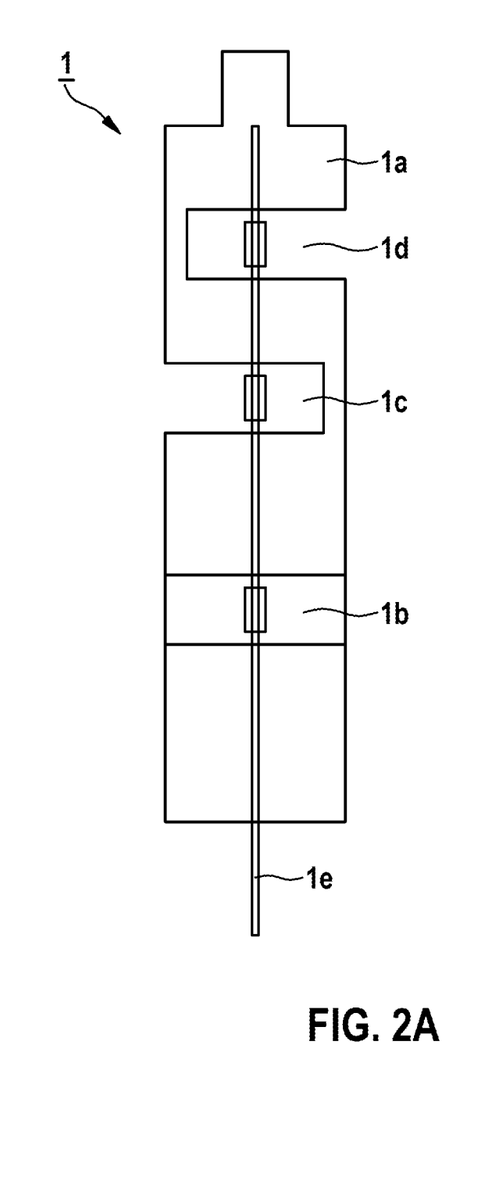
FIGS. 2A through 2C show detailed views of the sensor connection element according to FIG. 1.
Figure 2B:
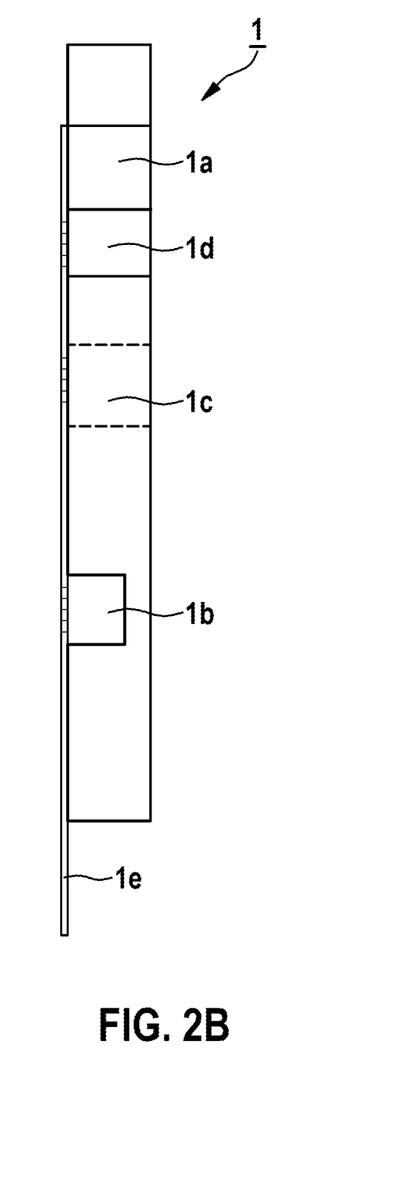

FIGS. 2A and 2B show the force transducer 1, which consists of the substrate 1a and the FBG sensor 1e, in slightly more detail. It can be seen that the three sensor regions (not denoted separately by reference numerals) of the FBG fiber 1e acting as sensor regions are each assigned in terms of position to one of the recesses 1b, 1c, 1d of the substrate 1a, said recesses being cuboidal or being rectangular in cross section. The structure and mode of operation of such an individual-fiber FBG sensor (also referred to hereinafter as an FBG fiber) are known from EP Patent No. 2 491 883 and do not require a more detailed description herein. Special features, however, are provided in conjunction with the planar substrate 1a compared with previously known cylindrical arrangements and will be explained further below. Compared with cylindrical substrate constructions, the planar substrate 1a has considerable advantages in terms of manufacture; in particular, it can be produced efficiently and cost-effectively using etching techniques known per se or XY-controlled microfibers in accordance with known micro structuring techniques.

Figure 2C:
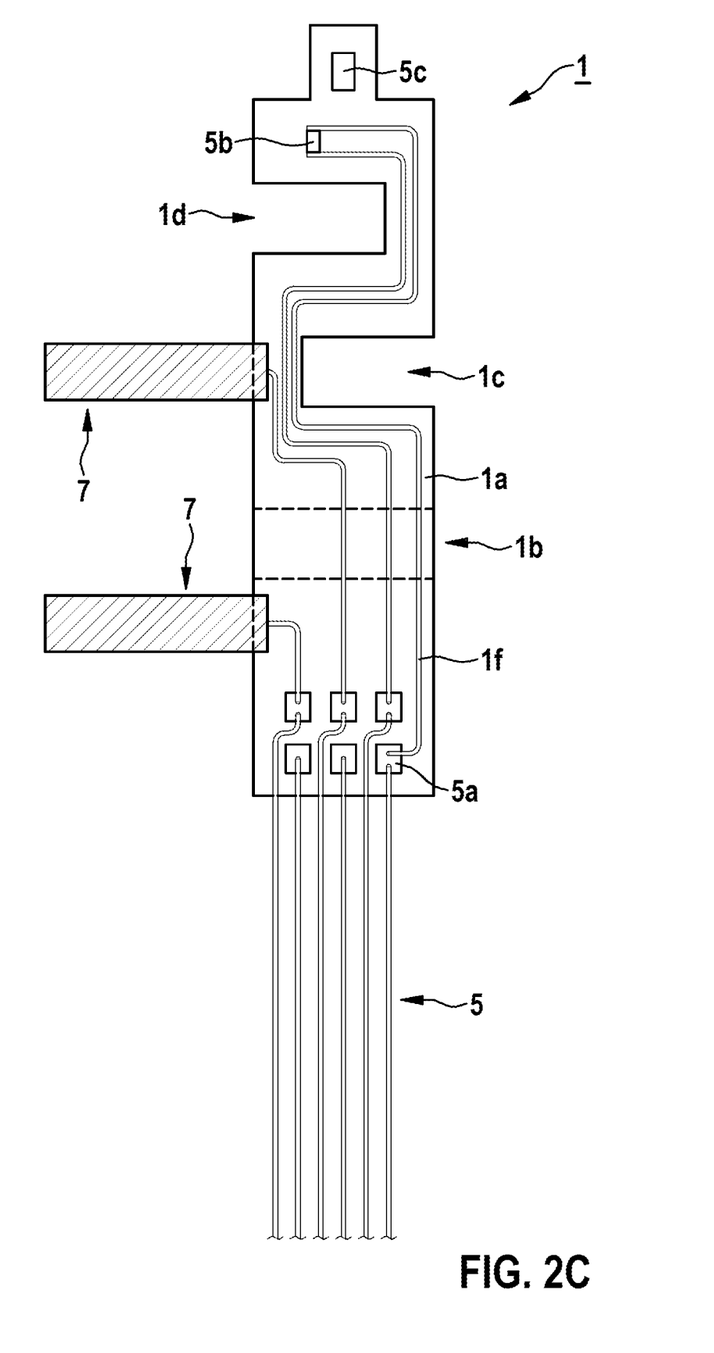

FIG. 2C shows a rear-side wiring of the force transducer 1 (without the FGB fiber 1e) by way of example and purely schematically for connection of the conductor faces 7, and also two distal contact faces 5b, 5c, which can be provided, for example, for the power supply of specific electronic component parts (not illustrated) or for the connection of an ablation electrode. Here, no feed lines to the contact face 5c can be seen; such lines can be arranged, in particular, in a second wiring layer arranged beneath the substrate surface. However, it is also possible in principle to provide further lines on the surface that can be seen here, by means of which lines the contact face 5c would be connected to additional proximal contact faces 5a.

The conductor tracks between the conductor lugs 7 and the distal contact face 5b and the proximal contact faces 5a can be provided using methods known per se from circuit board and/or semiconductor technology; that is to say using photolithographic structuring, coating and etching processes or using thick-film technology or the like. Here, a further substantial advantage of the present invention is provided, specifically the fact that developed and highly productive planar coating and structuring processes can be used.

In view of the fact that a highly accurate force measurement requires the knowledge of sensor-specific or catheter-specific data of the individual product in an enclosed evaluation unit, the catheter in accordance with a further exemplary embodiment of the present invention has an information carrier, arranged, in particular, at or in the vicinity of a proximal end and containing specific calibration information. In one exemplary embodiment, the information carrier is formed as an RFID tag or barcode, which can be easily and reliably read using cost-effective means, which are known per se, at the signal processing unit.

For the calculation of a 3D force vector, a calibration of the sensor system must take place, in which the sensor is subjected successively to three forces (Fx, Fy, Fz) perpendicular to one another.

In theory, the strains $\epsilon_1$, $\epsilon_2$ and $\epsilon_3$ in the distributed sensor regions having the flexural rigidities EI, the bending moments Fl and the distance r to the strain-neutral fiber are calculated as follows (FIG. 1):

$$\epsilon_1 = \frac{F_x \cdot l_1}{E \cdot l_{xx1}} \cdot r_{11} + \frac{F_y \cdot l_1}{E \cdot l_{yy1}} \cdot r_{12} + \frac{F_z}{A \cdot E} \quad \text{Eq. 1}$$

$$\epsilon_2 = \frac{F_x \cdot l_2}{E \cdot l_{xx2}} \cdot r_{21} + \frac{F_y \cdot l_2}{E \cdot l_{yy2}} \cdot r_{22} + \frac{F_z}{A \cdot E}$$

$$\epsilon_3 = \frac{F_x \cdot l_3}{E \cdot l_{xx3}} \cdot r_{31} + \frac{F_y \cdot l_3}{E \cdot l_{yy3}} \cdot r_{32} + \frac{F_z}{A \cdot E}$$

With three measurements, in which three forces perpendicular to one another are used, a corresponding calibration matrix can be calculated:

$$\begin{pmatrix} C_{11} & C_{12} & C_{13} \\ C_{21} & C_{22} & C_{23} \\ C_{31} & C_{32} & C_{33} \end{pmatrix} = \begin{pmatrix} F_x & 0 & 0 \\ 0 & F_y & 0 \\ 0 & 0 & F_z \end{pmatrix} \cdot \begin{pmatrix} \epsilon_{11} & \epsilon_{12} & \epsilon_{13} \\ \epsilon_{21} & \epsilon_{22} & \epsilon_{23} \\ \epsilon_{31} & \epsilon_{32} & \epsilon_{33} \end{pmatrix}^{-1} \quad \text{Eq. 2}$$

Here, the flexural rigidities EI and distances to the neutral fiber r in the sensor holder are such that three linearly independent equations are produced. It is thus possible to calculate a 3D force vector from measured strains of an arbitrary direction of force with the aid of the calibration matrix:

$$\begin{pmatrix} F_x \\ F_y \\ F_z \end{pmatrix} = \begin{pmatrix} C_{11} & C_{12} & C_{13} \\ C_{21} & C_{22} & C_{23} \\ C_{31} & C_{32} & C_{33} \end{pmatrix} \cdot \begin{pmatrix} \epsilon_1 \\ \epsilon_2 \\ \epsilon_3 \end{pmatrix} \quad \text{Eq. 3}$$

These calibration data are stored optionally in the catheter on an EEPROM, RFID or a 2D barcode and are read out from the evaluation unit wirelessly, in a wired manner, or, in the case of the 2D barcode, optically.

Figure 3A:
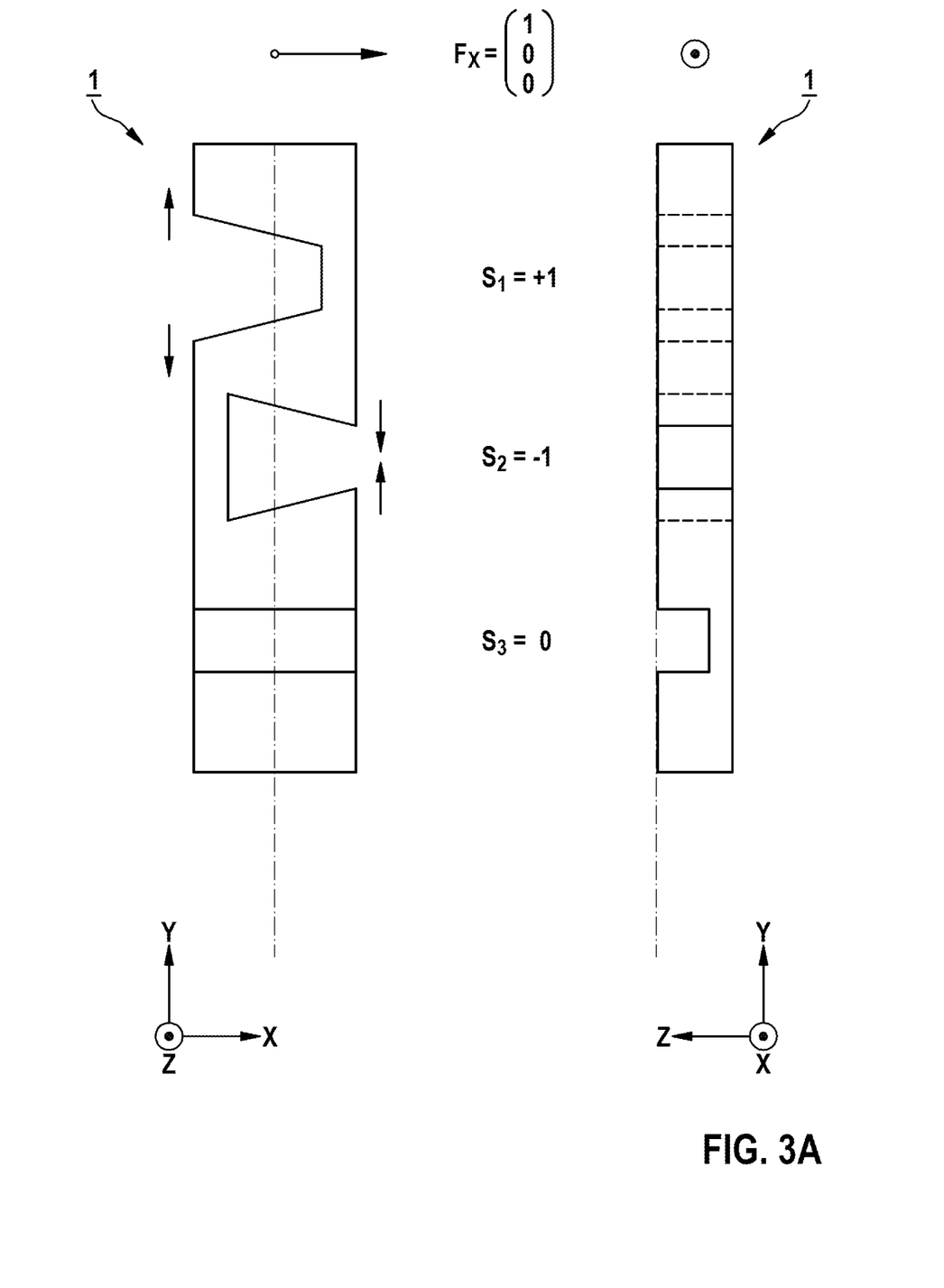
FIGS. 3A through 3C show schematic detailed views of the substrate of the sensor connection element (force transducer) in the rest state and with various exertions of force in order to explain the function and calibration.
Figure 3B:
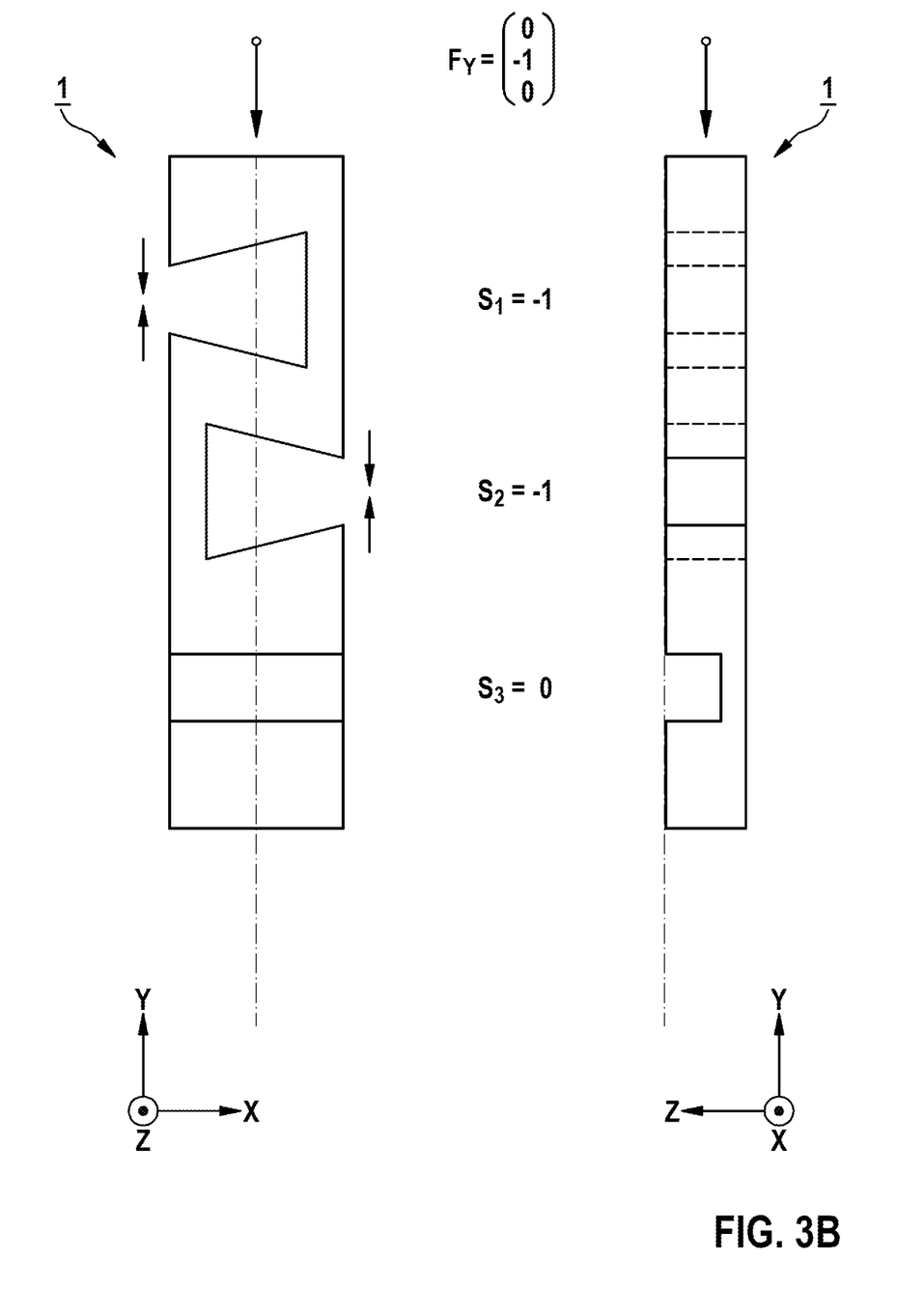
Figure 3C:
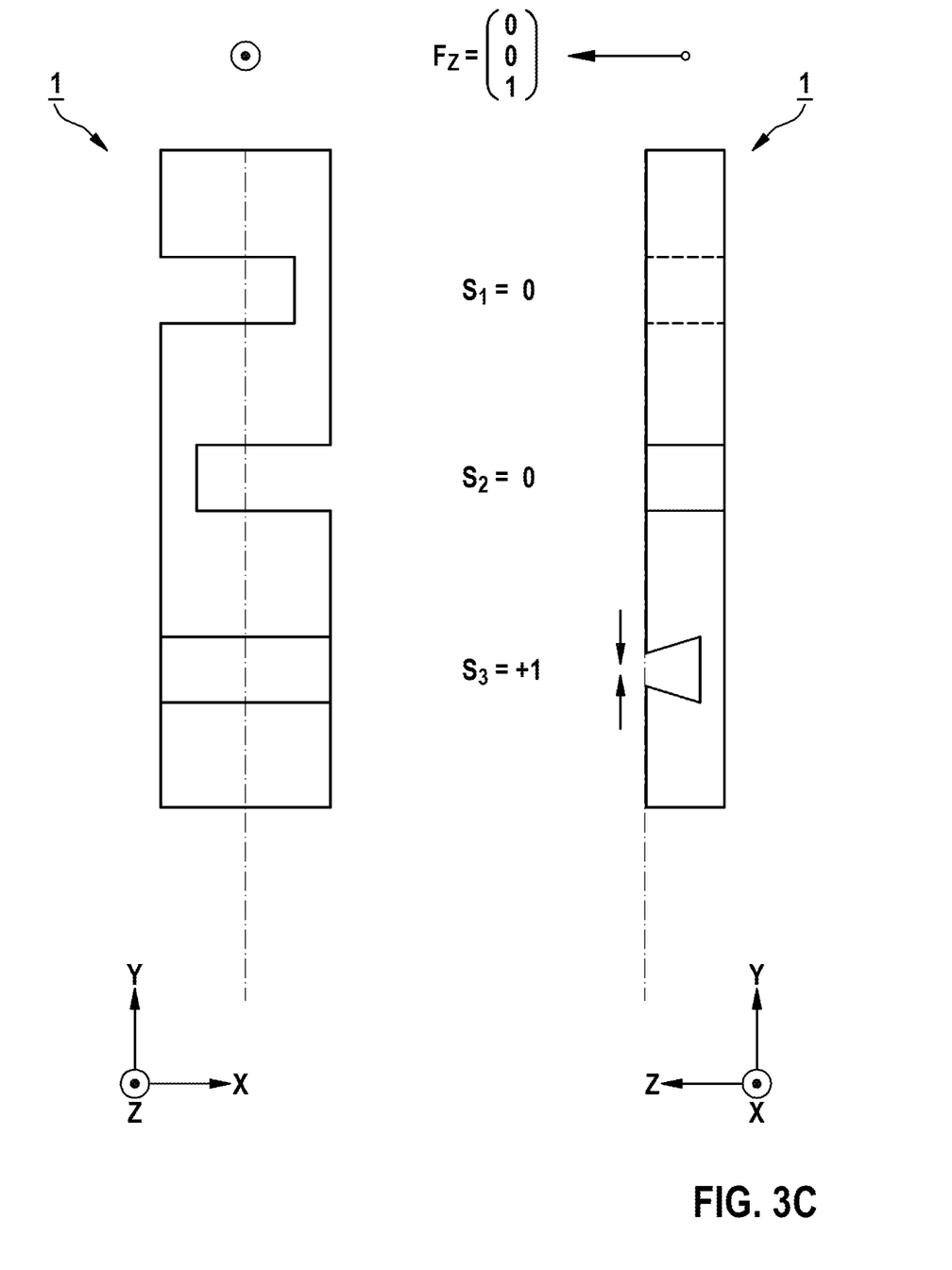

Hereinafter and with reference to FIGS. 3A to 3C, three case examples are provided in order to explain the calibration of a force transducer according to the invention. Case 1 (FIG. 3A) is a force $F_x$ consisting exclusively of X components; case 2 (FIG. 3B) is a force $F_y$ consisting exclusively of a Y component; and case 3 is a force $F_z$ consisting exclusively of a Z component. The deformation of the individual sensor regions $S_1$, $S_2$ and $S_3$ caused by respective force is indicated by arrows in the respective plan view and side view of the force transducer 1, and it is assumed that this deformation corresponds to a digital signal +1 or −1, whereas an undeformed sensor region provides the signal 0.

In case 1, equation 3 (with a swapping of the two sides) can be written (in the ideal case) as follows:

$$\begin{pmatrix} +1 \\ -1 \\ 0 \end{pmatrix} * \begin{pmatrix} 0.5 & -0.5 & 0 \\ 0.5 & 0.5 & 0 \\ 0 & 0 & -1 \end{pmatrix} = \begin{pmatrix} (0.5*1)+(-0.5*-1)+0 \\ (0.5*1)+(0.5*-1)+0 \\ (0*1)+(0*-1)+0 \end{pmatrix} = \begin{pmatrix} 1 \\ 0 \\ 0 \end{pmatrix} \quad \text{Eq. 3.1}$$

In case 2, the equation is as follows:

$$\begin{pmatrix} -1 \\ -1 \\ 0 \end{pmatrix} * \begin{pmatrix} 0.5 & -0.5 & 0 \\ 0.5 & 0.5 & 0 \\ 0 & 0 & -1 \end{pmatrix} = \quad \text{Eq. 3.2}$$

$$\begin{pmatrix} (0.5*-1)+(-0.5*-1)+0 \\ (0.5*-1)+(0.5*-1)+0 \\ (0*-1)+(0*-1)+0 \end{pmatrix} = \begin{pmatrix} 0 \\ -1 \\ 0 \end{pmatrix}$$

In case 3, the equation is as follows:

$$\begin{pmatrix} 0 \\ 0 \\ -1 \end{pmatrix} * \begin{pmatrix} 0.5 & -0.5 & 0 \\ 0.5 & 0.5 & 0 \\ 0 & 0 & -1 \end{pmatrix} = \quad \text{Eq. 3.3}$$

$$\begin{pmatrix} (0.5*0)+(-0.5*0)+(0*-1) \\ (0.5*0)+(0.5*0)+(0*-1) \\ (0*0)+(0*0)+(-1*-1) \end{pmatrix} = \begin{pmatrix} 0 \\ 0 \\ 1 \end{pmatrix}$$

In practice, it is assumed that the force components are transmitted unequally to the sensor regions; for example, the sensor region $S_1$ is thus more sensitive for example than $S_2$, and the sensor region $S_3$ is also sensitive for X and Y components of the effective force. In reality, there is generally a crosstalk between the sensor regions, that is to say each sensor region is also sensitive to a certain extent to effective forces that are oriented perpendicularly to the preferred axis of sensitivity of said sensor region. This is taken into consideration by means of a suitable coefficient matrix which, for example, may have the following form:

$$M = \begin{pmatrix} 0.2 & -0.8 & 0 \\ 0.2 & 0.8 & 0 \\ 0.1 & 0.1 & 0.8 \end{pmatrix} \quad \text{Eq. 4}$$

The exemplary embodiment of the present invention is not limited to the above-described examples and highlighted aspects, and a large number of modifications that lie within the capabilities of a person skilled in the art can also be made. By way of example, in the embodiment as a pure connection element (without the functionality of a strain gauge of the above-explained or a similar structure), recesses in the substrate can be used, for example, as conductor path interruptions or can be used to house circuits or also discrete electronic component parts in a space-saving and protected manner.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A sensor connection element of a catheter or an electrode line comprising:
    a plate-like substrate, comprising at least one recess and layer-like electrical conductors with sensor connection faces and/or actuator connection faces on or beneath at least one sensor surface,
    wherein the plate-like substrate is formed of a material that is rigid in compression and has at least one recess in both side edges, said recesses providing the sensor connection element with a predetermined flexural resilience.

2. The sensor connection element as claimed in claim 1, wherein the plate-like substrate is flat in the state of use.

3. The sensor connection element as claimed in claim 1, wherein the plate-like substrate is curved in the state of use into the shape of a hollow cylinder or hollow cylinder portion.

4. The sensor connection element as claimed in claim 1, wherein the plate-like substrate is multi-layered and has two or more levels, in which layer-like electrical conductors are arranged.

5. The sensor connection element as claimed in claim 1, wherein the plate-like substrate has at least one additional recess in at least one surface, said at least one additional recess providing the sensor connection element with a predetermined flexural resilience.

6. The sensor connection element as claimed in claim 5, wherein recesses that are offset relative to one another in the longitudinal direction of the substrate and that extend over the central line are provided in the side edges in such a way that the sensor connection element has a predetermined compressive resilience with respect to forces acting in the longitudinal direction.

7. The sensor connection element as claimed in claim 5, wherein the recess or at least one of a number of recesses has a rectangular or trapezoidal cross section.

8. The sensor connection element as claimed in claim 1, wherein the plate-like substrate comprises a metal or semiconductor material, including silicon, and/or a ceramic, including alumina ceramic, and/or a plastic material, including epoxy resin.

9. The sensor connection element as claimed in claim 6, wherein a Fiber Bragg Grating (FBG) sensor is fitted on the plate-like substrate so as to be arranged parallel to the side edges and is connected via the sensor connection faces in such a way that the sensor connection element forms a 3D force sensor.

10. The sensor connection element as claimed in claim 6, wherein the layer-like conductors are formed on the plate-like substrate and are selectively provided with additional functional elements in such a way that the sensor connection element forms an electric strain gauge.

11. A sensor connection element of a catheter or an electrode line comprising:
    a plate-like substrate, comprising at least one recess and layer-like electrical conductors with sensor connection faces and/or actuator connection faces on or beneath at least one sensor surface,
    wherein a conductor lug for providing a sensing and/or stimulation electrode of an electrode line is fitted on at least one actuator connection face.

12. A catheter comprising:
    a catheter body;

a sensor connection element as claimed in claim 1 embedded in the catheter body; and a sensor and/or actuator provided or connected by means of the sensor connection element.

13. An electrode line comprising:

a line body;

a sensor connection element as claimed in claim 1, embedded in the line body; and a sensor provided or connected by means of the sensor connection element and/or a sensing and/or stimulation or ablation electrode provided by means of the sensor connection element.

14. An electrode line comprising:

a line body;

a sensor connection element comprising:

a plate-like substrate, comprising at least one recess and layer-like electrical conductors with sensor connection faces and/or actuator connection faces on or beneath at least one sensor surface, wherein the plate-like substrate is formed of a material that is rigid in compression and has at least one recess in both side edges and in at least one surface, said recesses providing the sensor connection element with a predetermined flexural resilience, wherein recesses that are offset relative to one another in the longitudinal direction of the substrate and that extend over the central line are provided in the side edges in such a way that the sensor connection element has a predetermined compressive resilience with respect to forces acting in the longitudinal direction, wherein a Fiber Bragg Grating (FBG) sensor is fitted on the plate-like substrate so as to be arranged parallel to the side edges and is connected via the sensor connection faces in such a way that the sensor connection element forms a 3D force sensor, and wherein the line body is compressible and flexible in a distal portion, in which the sensor connection element is arranged, in such a way that it does not falsify the response of the 3D force sensor or strain gauge to external forces; and a sensor provided or connected by means of the sensor connection element and/or a sensing and/or stimulation or ablation electrode provided by means of the sensor connection element.

15. An electrode line comprising:

a line body;

a sensor connection element embedded in the line body, the sensor connection element comprising:

a plate-like substrate, comprising at least one recess and layer-like electrical conductors with sensor connection faces and/or actuator connection faces on or beneath at least one sensor surface; and at least one ring electrode, which is formed by winding a conductor lug, applied to an actuator connection face of the sensor connection element, around the line body.

* * * * *